United States Patent
Scheuren et al.

(10) Patent No.: US 9,511,158 B2
(45) Date of Patent: Dec. 6, 2016

(54) APPARATUS AND METHOD FOR THE STERILIZATION OF CONTAINERS WITH A SCREENING DEVICE AGAINST X-RAYS

(71) Applicant: KRONES AG, Neutraubling (DE)

(72) Inventors: Hans Scheuren, Bad Kreuznach (DE); Josef Knott, Schierling (DE); Michael Neubauer, Übersee (DE)

(73) Assignee: KRONES AG (DE)

( * ) Notice: Subject to any disclaimer, the term of this patent is extended or adjusted under 35 U.S.C. 154(b) by 55 days.

(21) Appl. No.: 14/274,478

(22) Filed: May 9, 2014

(65) Prior Publication Data

US 2014/0341353 A1 Nov. 20, 2014

(30) Foreign Application Priority Data

May 15, 2013 (DE) .................... 10 2013 104 998

(51) Int. Cl.
*A61L 2/00* (2006.01)
*A61L 2/08* (2006.01)
*B65B 55/08* (2006.01)

(52) U.S. Cl.
CPC ............. *A61L 2/082* (2013.01); *A61L 2/087* (2013.01); *B65B 55/08* (2013.01); *A61L 2202/12* (2013.01); *A61L 2202/23* (2013.01)

(58) Field of Classification Search
CPC .......... A61L 2/082; A61L 2/087; A61L 2/081; A61L 2/10; B65B 55/08
See application file for complete search history.

(56) References Cited

U.S. PATENT DOCUMENTS

| | | | |
|---|---|---|---|
| 2,336,443 A | 4/1941 | West | |
| 4,025,294 A | 5/1977 | Daane et al. | 432/11 |
| 6,285,030 B1 | 9/2001 | Williams et al. | 250/454.11 |
| 6,885,011 B2 | 4/2005 | Koenck et al. | 250/455.11 |
| 2010/0209290 A1 | 8/2010 | Cirri et al. | 422/22 |
| 2011/0012032 A1 | 1/2011 | Bufano et al. | 250/492.3 |
| 2011/0016829 A1 | 1/2011 | Drenguis et al. | 53/426 |

(Continued)

FOREIGN PATENT DOCUMENTS

| | | | | |
|---|---|---|---|---|
| DE | 10 2010 012 569 | 9/2011 | | A61L 2/08 |
| EP | 1 144 983 | 11/2004 | | G01N 21/00 |

(Continued)

OTHER PUBLICATIONS

Official Action issued in corresponding U.S. Appl. No. 14/461,148 dated Jul. 16, 2015 (15 pgs).

(Continued)

*Primary Examiner* — David J Makiya
*Assistant Examiner* — Dani Fox
(74) *Attorney, Agent, or Firm* — Hayes Soloway P.C.

(57) ABSTRACT

An apparatus for the sterilization of containers with a conveying device which conveys the containers along a pre-set conveying path, with at least one stressing device which acts upon the containers with radiation, for the purpose of the sterilization thereof, and with a screening device which screens off X-ray radiation which is formed in the context of the sterilization. The screening device has at least one outer wall which bounds the conveying path of the containers and which extends along the conveying path. The outer wall has at least one recess which forms a cavity which faces the conveying path of the containers in such a way that X-ray radiation formed during the sterilization can enter this cavity.

20 Claims, 4 Drawing Sheets

(56) References Cited

U.S. PATENT DOCUMENTS

| | | | |
|---|---|---|---|
| 2012/0042611 A1 | 2/2012 | Lappe | 53/426 |
| 2012/0219455 A1 | 8/2012 | Meinzinger et al. | 422/22 |
| 2012/0248659 A1 | 10/2012 | Neubauer et al. | 264/523 |
| 2013/0015365 A1 | 1/2013 | Bufano et al. | 250/454.11 |
| 2013/0129566 A1 | 5/2013 | Knott et al. | 422/22 |
| 2014/0112826 A1 | 4/2014 | Knott et al. | 422/22 |
| 2014/0231673 A1 | 8/2014 | Yokobayashi et al. | 250/455.11 |
| 2014/0299786 A1 | 10/2014 | Yokobayashi et al. | 250/455.11 |
| 2014/0369885 A1 | 12/2014 | Krueger | 422/22 |

FOREIGN PATENT DOCUMENTS

| | | | | |
|---|---|---|---|---|
| EP | 1982920 | 10/2008 | | B65B 55/08 |
| EP | 2 371 397 | 10/2011 | | A61L 2/08 |
| EP | 2 594 493 | 5/2013 | | A61L 2/08 |
| EP | 2 724 731 | 4/2014 | | A61L 2/08 |
| EP | 2 769 740 | 8/2014 | | A61L 2/08 |
| EP | 2 769 922 | 8/2014 | | A61L 2/08 |
| JP | 11-248892 | 9/1999 | | G21K 5/00 |
| WO | WO 2008/129397 | 10/2008 | | |
| WO | WO 2013/092735 | 6/2013 | | A61L 2/08 |

OTHER PUBLICATIONS

Extended European Search Report issued in corresponding European Patent Appln. No. 14001716.1-1356 dated Oct. 20, 2014 (6 pgs).

Extended European Search Report issued in corresponding European application, Feb. 5, 2015 (5 pgs).

First Office Action issued in corresponding Chinese Patent Appln. No. 2014101959805 dated May 5, 2016, with English translation (11 pgs).

German Search Report (no translation) issued in corresponding German Patent Appln. No. 20 2013 104 114.9 dated Jun. 20, 2014 (5 pgs).

APPARATUS AND METHOD FOR THE STERILIZATION OF CONTAINERS WITH A SCREENING DEVICE AGAINST X-RAYS

BACKGROUND OF THE INVENTION

The present invention relates to an apparatus and a method for the sterilization of containers. Various methods of this type are known from the prior art and are used for example to sterilize plastics material containers, and in particular plastics material pre-forms, before the further processing thereof. In this case sterilization methods, in which the plastics material containers are subjected to a sterilization agent such as for example hydrogen peroxide or peracetic acid, have long been known. In recent years, however, there has also been a shift towards using electromagnetic radiation, such as for example electron beams, ultraviolet rays or X-rays, for the sterilization. The use of beams of this type conserves resources to a greater degree on the one hand, since additional sterilization agent need not be used, but there is the drawback that hazardous radiation, such as for example ionizing radiation, in particular X-ray radiation, is frequently formed.

For this reason, screening devices are known from the prior art. At present, screens from ionizing radiation, such as for example X-ray radiation, are formed in sterilization plants, for example by rotating or jointly moved radiation separation elements which are arranged between the individual articles to be treated or which are formed by a tunnel-like arrangement of usually vertical separation elements, the dimensions of which depend upon the diameter with respect to the existing arc angle or upon the gap width. The drawback of jointly moved or jointly rotating separation elements of this type lies in the fact that aeration technology is influenced in different ways at different speeds. Furthermore, uncovering can also occur between the ejection faces or transfer faces and, as a result, undesired leaks in the case of rotating separating elements. In addition, in arrangements of this type it is difficult to seal off the beam from separating star wheels and directly at a radiation source of the processing star wheel. Even with narrow divisions between the individual articles to be sterilized, arrangements of this type are problematic. In addition, the assembly is also complicated and a hooking of lost containers can also occur. The provision of a beam tunnel leads to relatively long paths being necessary in part, in order to screen off the radiation. It has been found in this case that X-ray radiation is safe for humans only if it has been deflected or diverted respectively beforehand at least three times.

The object of the present invention is therefore to improve a screening with respect to ionizing radiation, such as in particular X-ray radiation, in the case of apparatus of this type. In addition, however, the outlay for screenings of this type should also be kept low. Ionizing radiation can be electron radiation, UV radiation or, in particular, X-ray radiation.

SUMMARY OF THE INVENTION

An apparatus according to the invention for the sterilization of containers has a conveying device which conveys the containers along a pre-set conveying path. Furthermore, the apparatus has at least one stressing device which acts upon the containers with a radiation, in particular an electromagnetic radiation, for the purpose of the sterilization thereof. Furthermore, the apparatus has a screening device which screens off (with respect to the environment) ionizing radiation, in particular X-ray radiation, which is formed in the context of the sterilization.

According to the invention the screening device has at least one outer wall which bounds the conveying path or a conveying region or conveying space respectively of the containers and which extends at least also along the conveying path, this outer wall having at least one recess which forms a cavity which faces the conveying path of the containers in such a way that X-ray radiation formed during the sterilization can enter or is capable of being directed into this cavity.

It is therefore proposed that a bounding outer wall of a conveying path or conveying region respectively should have formed in it recesses, also referred to below as beam traps, which have the effect that the X-ray radiation which is formed is reflected in them at least once and preferably several times, so that, as a result, the radiation is already decisively weakened, so that the screening as a whole can have smaller dimensions. In this way, the arc angle, which is required for the screening, can also be reduced. It is therefore proposed in order to obtain a shortening in this way and thus a reduction in the arc angle, so that beam traps may be used, in particular, on the outside. These beam traps operate in this case in such a way that an X-ray which could cover a maximum path in a processing tunnel, is not caused to be reflected on the outer wall of the tunnel, but is directed into an opening in the outer screening. This means that the containers are preferably conveyed inside a tunnel.

The beam cannot radiate again from this depression or the cavity respectively directly into the tunnel, but requires at least one further deflection for this. In this case it is preferable for the exposure or recess respectively to be slightly wider in the direction of an outer chamber in order to collect in a reliable manner all the radiation which is formed. In this way, as will be shown in greater detail below, it is possible for the recess to increase outwards for example starting from the outer wall. In addition, the depth of this recess or of the cavity respectively with the screening advantageously arranged downstream is advantageously selected in such a way that the beams striking a rear wall of the recess can also be directed back again into the tunnel only with at least one further deflection.

An angular dimension of this recess or beam trap respectively can be taken directly from the complete angle of the entire tunnel. This recess can also in this case, as described in greater detail below, be used at a second deflection.

By means of the recess according to the invention, angular reductions of 25° and more with respect to the tunnel can be achieved. It would also be possible, however, to prevent—in a cover or base region of the path or the walls which bound the conveying path respectively—X-ray radiation there from being reflected back again into the tunnel. Corresponding recesses, which are preferably made approximately the same size as those on a rear wall, can therefore also advantageously be provided in a region of a bounding base or the bounding cover respectively.

Although it would be possible for recesses of this type to be absent, it could also happen that reflecting radiation cancels out the function of the recess or the beam trap respectively at least in part, and this would mean that for example X-ray radiation would or could escape at an outlet window.

A shortening of the arc angle required for screening off the X-rays is made possible by the apparatus according to the invention and, in this way, a reduction in the necessary diameter of the star wheel can also be made possible, and this in turn means a reduction in the size of the housing. In addition, an effective sealing-off of the beams can be achieved, which with existing technology effects a sealing-off means of the beams which is arranged directly adjoining a beam-processing turntable. In this case no additional movements in a transfer star wheel are necessary in order to ensure the sealing tightness of the beams. In this way, it is also possible to dispense with the presence of rotating separation elements, as a result of which the apparatus as a whole is made simpler.

It is possible in this case for the recess to be designed completely in the form of a cavity. It would also be possible, however, for further radiation deflection elements, which likewise permit multiple reflection of the X-ray radiation inside the cavity, to be provided inside the cavity. In this way, it could be possible for the X-ray radiation to be reflected at least twice or even at least three times inside the cavity.

In the case of a further advantageous embodiment a geometrical structure of the recess is designed in such a way that the X-ray radiation is reflected several times at least in part on walls which bound the recesses. In addition, however, it would also be possible, as mentioned above, for further walls or reflecting members respectively of this type also to be provided inside the recess.

In the case of a further advantageous embodiment the conveying device has a rotatable carrier on which a plurality of holding devices for holding the containers are arranged. In this way, it is advantageous for the containers to be conveyed or transported respectively along a circular conveying path, in particular also during the sterilization thereof.

In the case of a further advantageous embodiment the stressing device has an electron radiation device which acts upon at least one wall region of the containers with electrons. In this case it is possible for this electron radiation device to act upon the containers from the outside for the sterilization thereof, but it would also be possible for the stressing device to have a rod-like body which is capable of being inserted into the containers through the aperture of the latter. In addition, a plurality of different types of stressing devices could also be provided. In this case it is possible and preferred for the stressing device to be arranged so as to be stationary and for the containers to move with respect to the latter. It would also be possible, however, for the stressing device itself to be arranged so as to be movable, and in particular movable with the containers.

In the case of a further advantageous embodiment the apparatus has a plurality of recesses which are arranged in succession along the conveying path of the containers. In this way, the circumferential angle which is necessary for the attenuation can be reduced still further. In this case it would also be possible for the recesses to be designed in such a way that for example the outer wall has a substantially corrugated structure. In addition, as mentioned above, recesses of this type can be arranged both in the aforesaid outer wall and in the cover or base wall. It is pointed out in this case that corresponding outer walls also constitute a cover wall and a base wall. In this way, these cover and base walls are also referred to more precisely below as the cover outer wall and the base outer wall respectively.

The inner wall, on the other hand, is that wall which is situated radially on the inside with respect to the conveying path of the containers and, in this way, bounds the conveying tunnel of the containers. The recesses described here can also be provided on the inner wall bounding the channel.

In the case of a further advantageous embodiment the apparatus therefore also has an inner wall which bounds the conveying path of the containers or the conveying region of the containers respectively and which preferably likewise extends in the direction of the conveying path. In this way, a conveying channel or conveying tunnel respectively is formed.

In the case of a further advantageous embodiment the beam traps are made movable with respect to the conveyed container units. If an increased reflection of stray radiation occurs at a container, then it is collected in the beam trap. In particular, in this case the counter-current conveying of the container unit and the beam trap should be taken into consideration. In order to reduce the necessary screening path further, the beam trap can be clock-timed point-wise to the reflecting container unit in such a way that the dose occurring periodically is intercepted at a measurement point. It would therefore also be possible for the beam traps themselves to be arranged so as to be movable. In this case both a movement of the beam traps in a conveying direction (or in a direction opposed to this conveying direction) of the containers is possible (at the same or a different speed) and a movement in directions deviating therefrom are possible. In this way, a wall on which the beam traps are arranged could also move for example.

In the case of a further advantageous embodiment the apparatus forms a clean room inside which the containers are conveyed during the sterilization thereof. In this case it is possible for an over-pressure to be present inside this clean room, so that no contamination can penetrate into the clean room from the outside. In addition, it would be possible for a sealing device to be provided which seals this clean room off from the environment. In this case it is possible for this sealing device to have two elements or wall portions respectively which are movable with respect to each other.

It would also be possible, however, for the containers to be sterilized not inside a clean room but for example before reaching a clean room. In this way for example, a pre-sterilization can be made possible which can reduce a subsequent main sterilization or after-sterilization respectively in terms of the outlay thereof.

The present invention further relates to a method of processing containers. In this case the containers are conveyed along a pre-set conveying path by means of a conveying device and the containers are acted upon with an electromagnetic radiation by means of at least one stressing device for the purpose of their sterilization, X-ray radiation being formed during this stressing and this X-ray radiation which is formed being screened off at least in part by means of a screening device. According to the invention the X-ray radiation arrives at least in part in a recess which is arranged in a wall, in particular an outer wall, bounding the conveying path of the containers.

In this way, it is also proposed in terms of the method that a recess is formed in the wall which serves to weaken the X-ray radiation, in particular by at least single and preferably multiple reflection of this X-ray radiation, inside the recess.

In the case of a preferred variant the containers are conveyed along a circular conveying path.

BRIEF DESCRIPTION OF THE DRAWINGS

Further advantages and embodiments are evident from the accompanying drawings. In the drawings

DETAILED DESCRIPTION OF THE INVENTION

Figure 1:
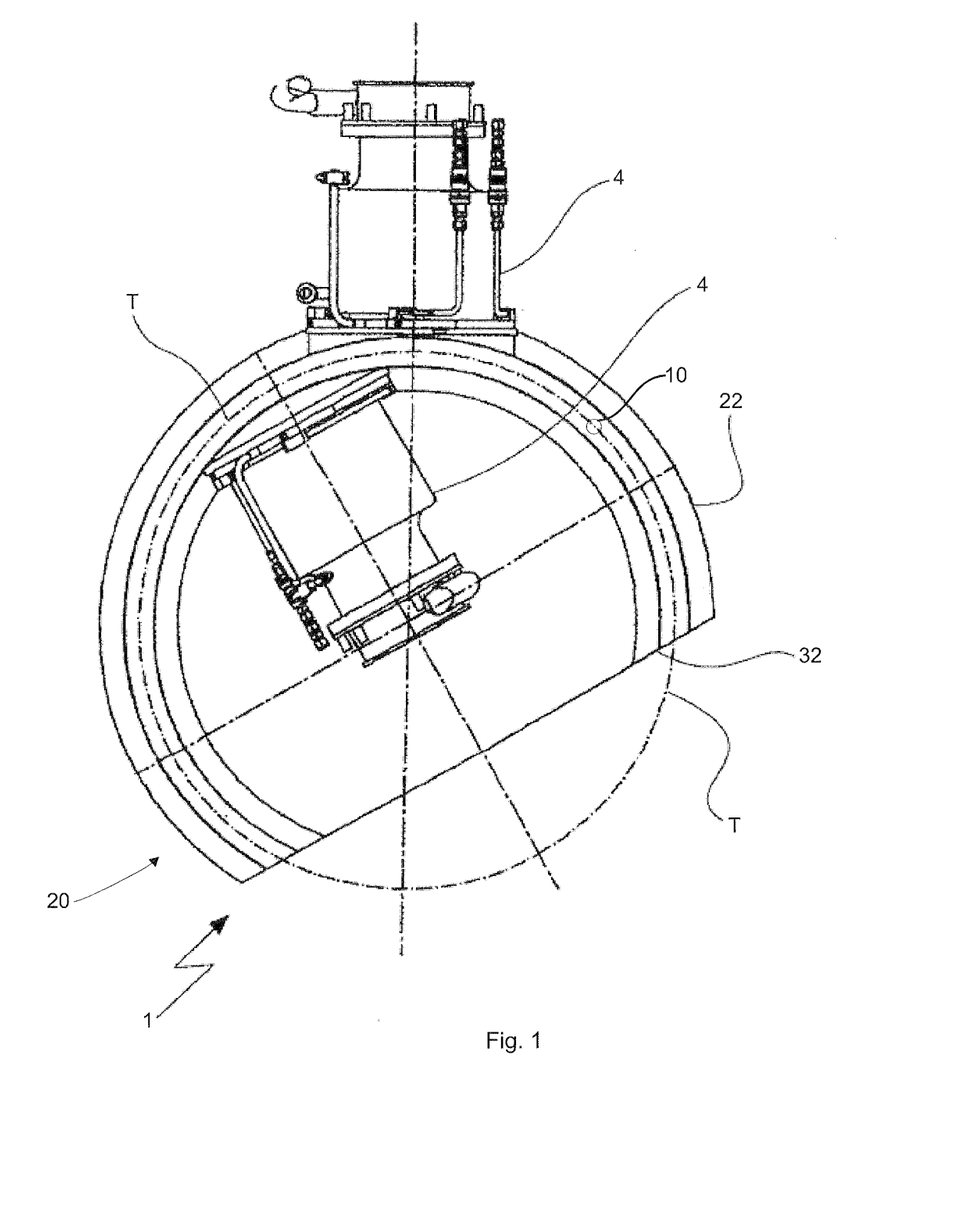
FIG. 1 is a diagrammatic illustration of an apparatus for the sterilization of containers according to the internal prior art of the Applicants.

FIG. 1 is a roughly diagrammatic illustration of an apparatus 1 for the sterilization of containers according to the internal prior art of the Applicants. In this case containers 10 (shown only diagrammatically) are conveyed between two walls 22 and 32 along a conveying path T which is circular here. The reference number 1 refers to the apparatus in its entirety. This apparatus has in this case two stressing devices or radiation devices 4 which act upon an outer wall of the containers with radiation, for example with electron radiation. A channel, inside which the plastics material pre-forms 10 are conveyed, is formed between the two walls 22 and 32 and a base wall (not shown).

The apparatus 1 has a conveying device (not shown) which conveys the containers. In this case it would be possible for a rotatable carrier to be provided on which are arranged gripping elements and/or holding mandrels for gripping or holding respectively the containers 10, which are in particular plastics material pre-forms. It would also be possible for the inner wall 32 to be arranged so as to be rotatable and for gripping elements or holding mandrels respectively to be arranged on this inner wall. The reference number 20 refers in its entirety to the screening device which screens off the X-ray radiation which is formed, in which case for example the outer wall is a component of this screening device 20.

The apparatus 1 shown is preferably arranged inside a module which has further processing stations, in particular one further processing station. The plastics material pre-forms preferably pass through the module in such a way that downstream of an inlet star wheel they are sterilized on the outside thereof by means of charge carrier radiation, in particular by means of electron beams (protons or a particles for example would also, however, be possible), by the apparatus 1 shown. During the external irradiation the plastics material pre-forms are preferably held on the inner face thereof by means of an inner gripper and are conveyed through a tunnel-like channel. After that, the plastics material pre-forms are preferably conveyed by means of an aseptic conveying star wheel or distribution star wheel respectively to a following processing apparatus (not shown) which disinfects the plastics material pre-forms (likewise preferably by means of electron radiation) on the inner side thereof.

In this case the plastics material pre-forms are held on the outside thereof, whilst an electron beam emitter is introduced at least in part into the pre-form. A relative movement between the emitter and the container or the pre-form respectively takes place during this internal disinfection. After the internal disinfection the pre-forms are conveyed out of the module by means of a further conveying star wheel. The aforesaid apparatus inside the module are preferably enclosed in their entirety in this case, so that no electron or X-ray radiation can escape. In particular, it is also possible therefore for beam traps, which ensure the frequent deflection of the X-ray radiation inside the module, to be arranged inside this module enclosure, so as to be able to keep the module compact.

Figure 2:
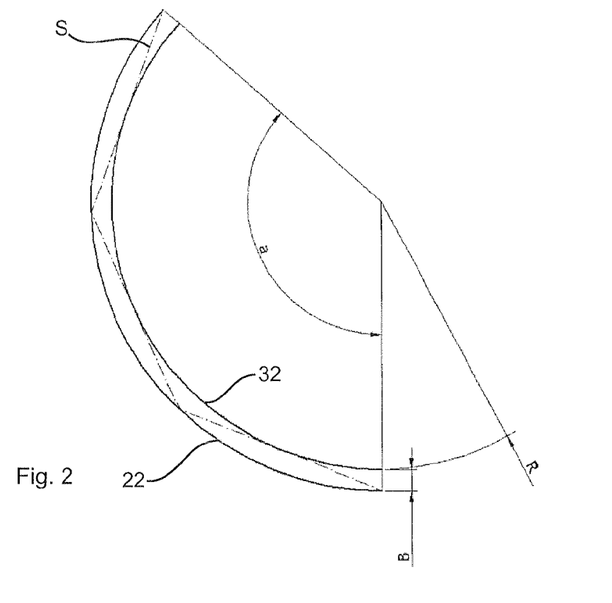
FIG. 2 is a diagrammatic illustration to demonstrate the pattern of X-rays in the apparatus as shown in FIG. 1.

FIG. 2 is an illustration to demonstrate a radiation pattern in the case of the apparatus shown in FIG. 1. In this case the reference letter S refers to X-ray radiation which is formed and which is reflected several times here and is weakened in this way. The reference letter a designates an arc which corresponds to that peripheral angle which is necessary to achieve an adequate attenuation of the X-ray radiation. This is formed from the angle which is present between three points at which the radiation is reflected three times on the outer wall. The reference letter B designates the distance between the two walls 22 and 32 and thus the width of the gap inside which the plastics material pre-forms 10 are conveyed. The reference letter R designates a radius of curvature of the inner wall 32. It will be seen that the two walls are curved in a circular manner here and preferably have as their centre in each case the centre of the conveying path of the plastics material pre-forms.

Figure 3:
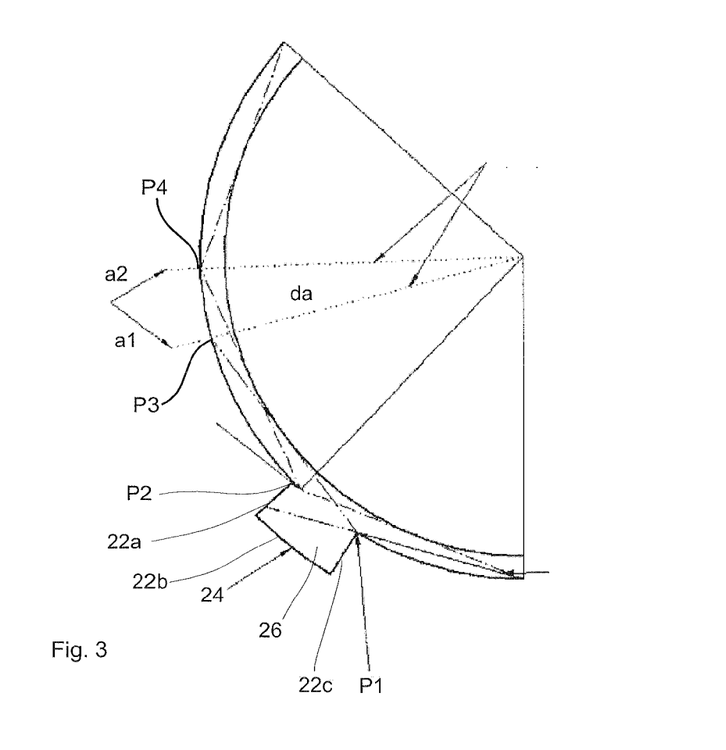
FIG. 3 is a diagrammatic illustration of an apparatus according to the invention.

FIG. 3 is a diagrammatic illustration of the apparatus according to the invention. In the case of this arrangement a recess 24 or a beam trap 24 respectively is arranged on the outer wall 22. This recess forms a cavity 26, into which the X-rays S can enter. In addition, this recess 24 has a cross-section which is enlarged radially towards the outside. As a result of this cross-section the efficiency of the recess or the beam trap 24 respectively can be further improved. The references 22a, 22b, 22c refer to walls which bound the cavity and on which the X-ray radiation which is formed can likewise be reflected. In addition, it would also be possible, in a manner dependent upon the dimensions of the recess, for X-ray radiation which is formed to be reflected in succession at a plurality of these walls 22a, 22b, 22c. The reference da again designates the angular difference which results from the two angles a2 and a1 and which demonstrates the reduction which is achieved by the introduction of the beam trap 24.

Figure 4:
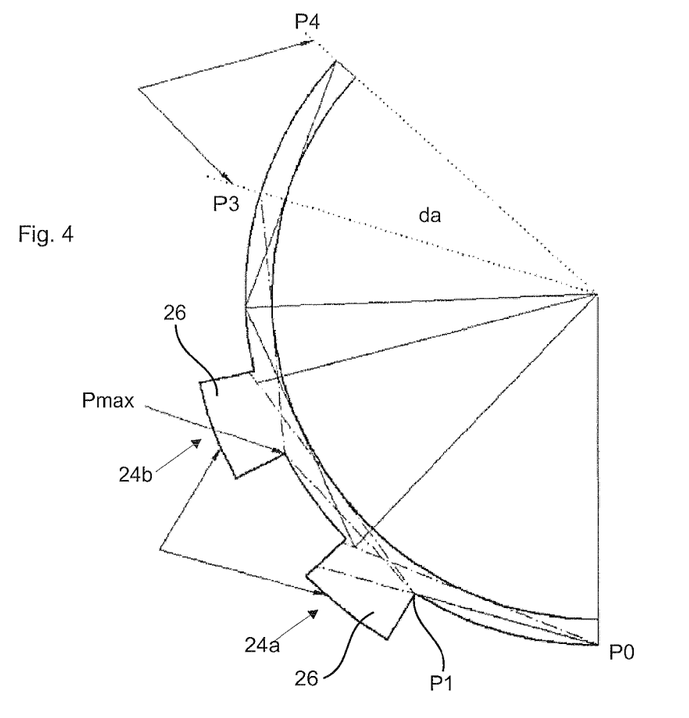
FIG. 4 shows a further embodiment of the apparatus according to the invention.

FIG. 4 shows a further embodiment of the apparatus according to the invention. In the case of this embodiment two recesses 24a, 24b, which in each case form the cavities 26, are arranged on or in the outer wall. The reference da designates the angle or the peripheral path respectively which can be saved by the existence of these two recesses or beam traps respectively. In this case the reference P4 relates to the point at which the beams starting from the point P0 (entry of the beams) are reflected for the third time. The reference 53 designates the point which the beams can reach at most in the presence of the two beam traps, the point Pmax of the respective maximum reflection point with the beam trap being designated in each case by the reference Pmax.

Figure 5:
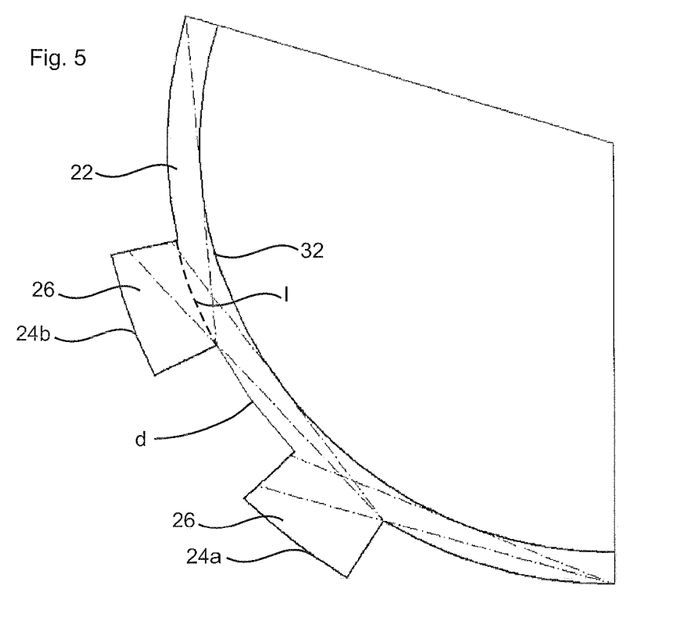
FIG. 5 shows a beam pattern in the case of the apparatus from FIG. 4.

FIG. 5 shows a beam pattern in the case of the apparatus from FIG. 4, in which case only the beam patterns are indicated which can occur at a maximum in the presence of the two recesses. It is advantageous for the recesses 24a, 24b to be arranged at a pre-set distance from each other in a peripheral direction of the apparatus 1. In this case this distance can also be selected in a manner dependent upon a peripheral dimension of the respective recess in such a way that a maximum beam path of the X-ray radiation which is formed is reduced in an optimum manner. It is preferable for a ratio between a length l of the two recesses 24a, 24b in the peripheral direction and a distance d between these adjacent recesses to be between 1:2 and 2:1, preferably between 1:1.5 and 1.5:1 and in a particularly preferred manner between 1:1.2 and 1.2:1.

Figure 6:
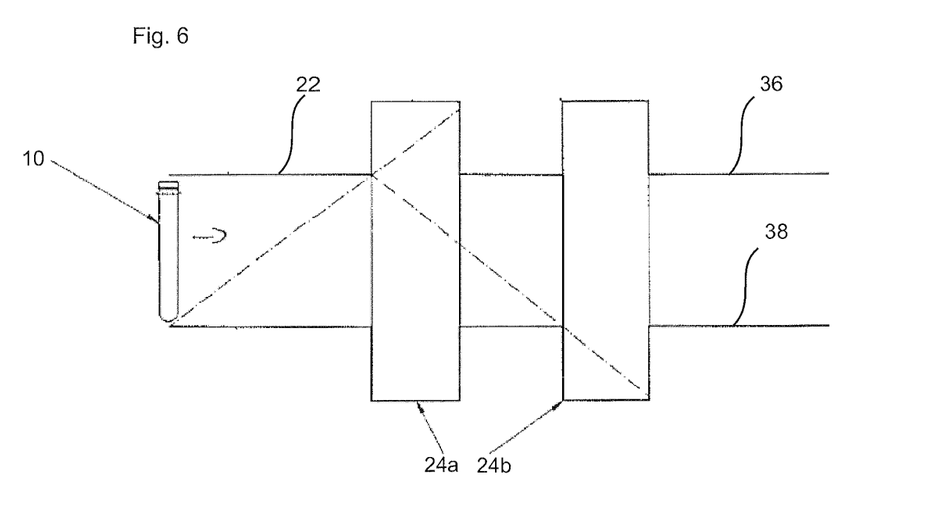
FIG. 6 shows a further embodiment of the present invention.

FIG. 6 is a side view of a further embodiment of the apparatus according to the invention. It is evident in this case that corresponding recesses are also present in a cover wall 36 and a base wall 38. In this way, it would be possible for the recesses 24 or 24a, 24b respectively described above to be designed in such a way that they also extend into the region of the cover wall and/or the base wall. It is evident that a shortening of the path to be covered at most by the radiation can also be achieved as far as the third reflection by these steps.

It is advantageous for the walls to be produced at least in part and preferably completely from a material which screens off X-rays, such as for example lead.

In addition, it would also be possible and preferred for the radiation devices 4 shown in FIG. 1 to be arranged in such a way that in all events radiation cannot reach as far as an outlet separation device and/or an inlet separation device of the apparatus.

The Applicants reserve the right to claim all the features disclosed in the application documents as being essential to the invention, insofar as they are novel either individually or in combination as compared with the prior art.

LIST OF REFERENCES 1 apparatus in its entirety
4 radiation devices
10 containers
20 screening device
22, 32 walls
22a, 22b, 22c walls
24 recess/beam trap
24a, 24b recesses
26 cavity
32 inner wall
36 cover wall
38 base wall
T circular conveying path
S X-ray radiation
B width of the gap
R radius of the inner wall 32
a arc
a1, a2 angles
da angular difference
P0 to P5 points
l length of the recess in the peripheral direction
d distance between two recesses in the peripheral direction

The invention claimed is:

1. An apparatus for the sterilization of a plurality of containers comprising:
a conveying device which conveys the containers along a pre-set conveying path,
at least one stressing device which acts upon the containers with x-ray or electron beam radiation to sterilize the plurality of containers, and
a screening device which screens off secondary x-ray radiation formed by the at least one stressing device during sterilization, wherein the screening device has at least one outer wall which bounds the pre-set conveying path of the plurality of containers and which extends along the pre-set conveying path, and the outer wall has at least one recess which forms a cavity which faces the pre-set conveying path of the plurality of containers in such a way that second x-ray radiation formed during sterilization enters the cavity, wherein the at least one recess comprises a geometrical structure that reflects the secondary x-ray radiation a plurality of times at least in part on a plurality of recess walls which bound the at least one recess, wherein the at least one recess prevents a beam of the secondary x-ray radiation radiated from a container of the plurality of containers from being reflected on an outer wall of a processing tunnel, wherein the beam is directed into the at least one recess such that the beam cannot radiate again from the at least one recess directly into the tunnel, and wherein the beam requires at least one further deflection to radiate into the processing tunnel.

2. An apparatus according to claim 1, wherein the conveying device has a rotatable carrier on which a plurality of holding devices for holding the containers are arranged.

3. An apparatus according to claim 1, wherein the stressing device has an electron radiation device which acts upon at least one wall region of the containers with electrons.

4. An apparatus according to claim 1, wherein the apparatus has a plurality of recesses which are arranged in succession along the conveying path of the containers.

5. An apparatus according to claim 4, wherein the recesses are designed in such a way that the outer wall has a substantially corrugated structure.

6. An apparatus according to claim 5, wherein recesses are arranged both in the outer wall and in the cover or base wall.

7. An apparatus according to claim 1, wherein the apparatus has an inner wall which bounds the conveying path of the containers and which extends in the direction of the conveying path.

8. An apparatus according to claim 1, wherein the apparatus includes a clean room inside which the containers are conveyed during the sterilization thereof.

9. An apparatus according to claim 1, wherein the recess is designed completely in the form of a cavity.

10. An apparatus according to claim 1, wherein further radiation deflection elements, which permit multiple reflection of the ionizing radiation inside the cavity, are provided inside the cavity.

11. An apparatus according to claim 10, wherein the ionizing radiation is reflected at least twice inside the cavity.

12. An apparatus according to claim 10, wherein the ionizing radiation is reflected at least three times inside the cavity.

13. An apparatus according to claim 1, wherein the stressing device is arranged stationary and the containers move with respect to the latter.

14. An apparatus according to claim 1, wherein the stressing device itself is arranged movable and movable with the containers.

15. An apparatus according to claim 1, wherein the recesses are designed as a beam trap.

16. An apparatus according to claim 15, wherein the beam traps are moveable with respect to the conveying container units.

17. A method of processing a plurality of containers, comprising the steps of:
conveying the plurality of containers along a pre-set conveying path by a conveying device, and
acting upon the plurality of containers with x-ray or electron beam radiation by at least one stressing device to sterilize the plurality of containers, wherein secondary x-ray radiation is formed by the at least one stressing device acting upon the plurality of containers during sterilization, and screening off the secondary x-ray radiation by a screening device, wherein the secondary x-ray radiation arrives at least in part in at least one recess which is arranged in a wall bounding the pre-set conveying path of the plurality of containers, wherein the at least one recess comprises a geometrical structure that reflects the secondary x-ray radiation a plurality of times at least in part on plurality of recess walls which hound the at least one recess, wherein the at least one recess prevents a beam of the secondary x-ray radiation from a container of the plurality of containers from being reflected on an outer wall of a processing tunnel wherein the beam is directed into the at least one recess such that the beam cannot radiate again from the at least one recess directly into the tunnel, and wherein the beam requires at last one further deflection to radiate into the processing tunnel.

18. A method according to claim 17, wherein the containers are conveyed along a circular conveying path.

19. A method according to claim 17, wherein the recess is formed in the wall which serves to weaken the ionizing radiation by at least single reflection of the ionizing radiation, inside the recess.

20. A method according to claim 17, wherein the recess is formed in the wall which serves to weaken the ionizing radiation by multiple reflections of the ionizing radiation, inside the recess.

* * * * *

UNITED STATES PATENT AND TRADEMARK OFFICE
CERTIFICATE OF CORRECTION

PATENT NO. : 9,511,158 B2
APPLICATION NO. : 14/274478
DATED : December 6, 2016
INVENTOR(S) : Scheuren et al.

Page 1 of 1

It is certified that error appears in the above-identified patent and that said Letters Patent is hereby corrected as shown below:

Claim 17, Column 9, Line 8, "hound" should be --bound--.

Signed and Sealed this
Thirty-first Day of July, 2018

Andrei Iancu
*Director of the United States Patent and Trademark Office*